(12) United States Patent
Lunn et al.

(10) Patent No.: US 9,386,977 B2
(45) Date of Patent: Jul. 12, 2016

(54) COMPOSITE ANCHOR

(71) Applicant: Richard M. Lunn, Kingston, MA (US)

(72) Inventors: Richard M. Lunn, Kingston, MA (US); David A. Paulk, Hopedale, MA (US)

(73) Assignee: Smith & Nephew, Inc., Memphis, TN (US)

( * ) Notice: Subject to any disclaimer, the term of this patent is extended or adjusted under 35 U.S.C. 154(b) by 138 days.

(21) Appl. No.: 14/275,399

(22) Filed: May 12, 2014

(65) Prior Publication Data

US 2014/0343605 A1  Nov. 20, 2014

Related U.S. Application Data

(62) Division of application No. 12/632,220, filed on Dec. 7, 2009, now Pat. No. 8,771,315.

(60) Provisional application No. 61/122,512, filed on Dec. 15, 2008.

(51) Int. Cl.
*A61B 17/04* (2006.01)

(52) U.S. Cl.
CPC ....... *A61B 17/0401* (2013.01); *A61B 2017/044* (2013.01); *A61B 2017/0445* (2013.01); *A61B 2017/0448* (2013.01); *A61B 2017/0451* (2013.01); *A61B 2017/0458* (2013.01); *A61B 2017/0464* (2013.01)

(58) Field of Classification Search
CPC .......... A61B 17/0401; A61B 2017/0451; A61B 2017/0464; A61B 2017/044; A61B 2017/0458; A61B 2017/0448; A61B 2017/0445
See application file for complete search history.

(56) References Cited

U.S. PATENT DOCUMENTS

| | | | |
|---|---|---|---|
| 4,537,185 A | 8/1985 | Stednitz | |
| 4,870,957 A | 10/1989 | Goble et al. | |
| 5,370,662 A | 12/1994 | Stone et al. | |
| 5,383,905 A | 1/1995 | Golds et al. | |
| 5,417,712 A | 5/1995 | Whittaker et al. | |
| 5,470,334 A | 11/1995 | Ross et al. | |
| 5,505,735 A | 4/1996 | Li | |
| 5,584,835 A | 12/1996 | Greenfield | |
| 5,733,307 A | 3/1998 | Dinsdale | |
| 5,935,129 A | 8/1999 | McDevitt | |

(Continued)

FOREIGN PATENT DOCUMENTS

| | | |
|---|---|---|
| EP | 1584297 A1 | 10/2005 |
| JP | 2000-166937 | 6/2000 |

(Continued)

OTHER PUBLICATIONS

Third Office Action for Chinese patent application No. 200980150612.6, dated Mar. 31, 2014.

(Continued)

*Primary Examiner* — Julian W Woo
(74) *Attorney, Agent, or Firm* — Burns & Levinson LLP; Joseph M. Maraia

(57) ABSTRACT

The present disclosure relates to a composite anchor. The anchor includes a cannulated proximal portion having a threaded outer surface and a distal portion coupled to the proximal portion, the distal portion including a top portion, a bottom portion, and a through hole, wherein the top portion is configured to be disposed within the cannulation of the proximal portion.

20 Claims, 7 Drawing Sheets

(56) References Cited

U.S. PATENT DOCUMENTS

| | | |
|---|---|---|
| 5,948,001 A | 9/1999 | Larsen |
| 5,957,953 A | 9/1999 | DiPoto |
| 5,993,459 A | 11/1999 | Larsen et al. |
| 6,436,124 B1 | 8/2002 | Anderson et al. |
| 6,517,542 B1 | 2/2003 | Papay et al. |
| 6,840,953 B2 | 1/2005 | Martinek |
| 6,916,321 B2 | 7/2005 | TenHuisen et al. |
| 6,923,824 B2 | 8/2005 | Morgan et al. |
| 7,588,587 B2 | 9/2009 | Barbieri et al. |
| 7,828,820 B2 | 11/2010 | Stone et al. |
| 7,976,565 B1 | 7/2011 | Meridew |
| 8,663,279 B2 * | 3/2014 | Burkhart ............ A61B 17/0401 606/232 |
| 2001/0049528 A1 | 12/2001 | Kubota |
| 2002/0052629 A1 | 5/2002 | Morgan et al. |
| 2002/0147463 A1 | 10/2002 | Martinek |
| 2004/0138706 A1 | 7/2004 | Abrams et al. |
| 2004/0210227 A1 | 10/2004 | Trail et al. |
| 2006/0149258 A1 | 7/2006 | Sousa et al. |
| 2006/0276841 A1 | 12/2006 | Barbieri et al. |
| 2006/0282081 A1 | 12/2006 | Fanton et al. |
| 2007/0161985 A1 | 7/2007 | Demakas et al. |
| 2007/0225719 A1 | 9/2007 | Stone et al. |
| 2007/0250064 A1 | 10/2007 | Darois et al. |
| 2008/0009904 A1 | 1/2008 | Bourque et al. |
| 2008/0154313 A1 | 6/2008 | Berberich |
| 2008/0208253 A1 | 8/2008 | Dreyfuss et al. |
| 2008/0215091 A1 | 9/2008 | Dreyfuss |
| 2008/0275469 A1 | 11/2008 | Fanton et al. |
| 2009/0112270 A1 | 4/2009 | Lunn et al. |
| 2009/0157124 A1 | 6/2009 | Ferragamo et al. |
| 2010/0016869 A1 | 1/2010 | Paulk et al. |
| 2010/0016902 A1 | 1/2010 | Paulk et al. |
| 2010/0130989 A1 | 5/2010 | Bourque et al. |
| 2010/0152773 A1 | 6/2010 | Lunn et al. |
| 2010/0217329 A1 | 8/2010 | Brown |

FOREIGN PATENT DOCUMENTS

| | | |
|---|---|---|
| JP | 2001514545 A | 9/2001 |
| JP | 2005-103272 | 4/2005 |
| JP | 2008-029746 | 2/2008 |
| WO | 92/03979 | 3/1992 |
| WO | 9203979 A1 | 3/1992 |
| WO | 02/21997 A2 | 3/2002 |
| WO | 02/051325 A2 | 7/2002 |
| WO | 2006/099109 A2 | 9/2006 |
| WO | 2007/078281 A2 | 7/2007 |
| WO | 2009/055800 A1 | 4/2009 |

OTHER PUBLICATIONS

Patent Examination Report No. 1 dated Aug. 17, 2015 issued by IP Australia for Australian Patent Application No. 2012230845.
First Office Action for related Chinese patent application No. 201280014306.1, issued Aug. 3, 2015.
Substantive Examination for related Mexico Patent Application No. MX/a/2013/010810 mailed Aug. 25, 2015.
Patent Examination Report No. 1 dated Sep. 30, 2014 issued by IP Australia for Australian Patent Application No. 2009327446.
Appeal Decision for Japanese Patent Application No. 2014-21937 mailed Nov. 16, 2015.
Decision of Rejection for Japanese patent application No. 2011-540802, dated Jul. 2, 2014.
First Office Action for Japanese patent application No. 2011-540802, dated Dec. 24, 2013.
Second Office Action for Chinese patent application No. 200980150612.6, dated Dec. 18, 2013.
Communication pursuant to Article 94(3) EPC Oct. 4, 2014.
International Search Report and Written Opinion for PCT/US2012/030095 Dated Jan. 20, 2010.
International Search Report and Written Opinion for PCT/US2009/066966 Dated May 21, 2012.
Communication pursuant to ARticle 94(3) EPC from related European Application No. 09771445.5 dated Apr. 4, 2016.
Patent Examination Report No. 2 for related Australian Application No. 2012230845 issued Apr. 6, 2016.
Notice of Reasons for Rejection for related Japanese Application No. 2014-501237 mailed Jan. 18, 2016.
Substantive Examination of related Mexican Application No. MX/a/2013/010810 mailed Jan. 28, 2016.
Second Office Action from related Chinese Application No. 201280014306.1 issued Mar. 28, 2016.

* cited by examiner

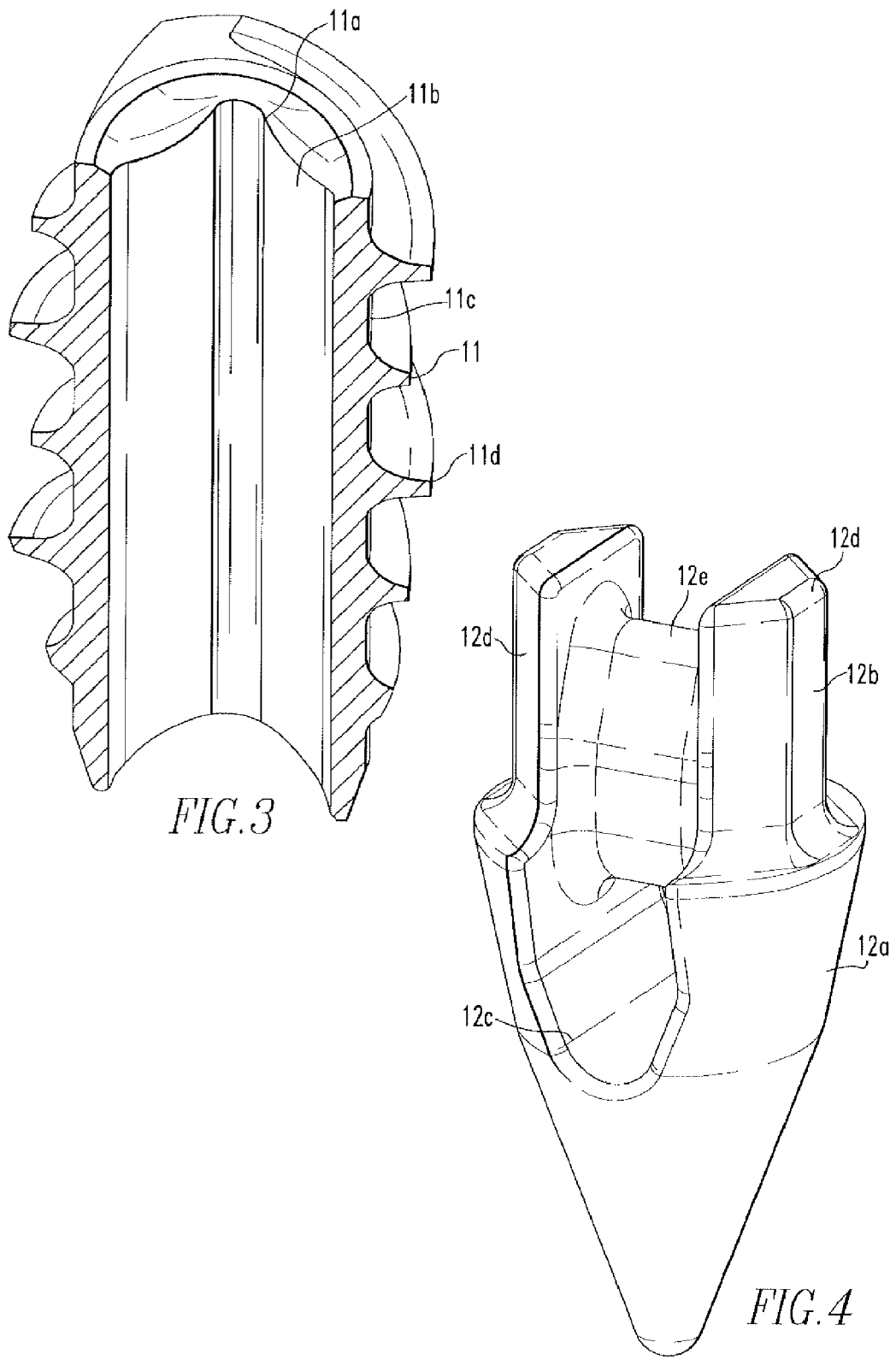

COMPOSITE ANCHOR

CROSS-REFERENCE TO RELATED APPLICATIONS

This application is a Divisional application of U.S. patent application Ser. No. 12/632,220 filed on Dec. 7, 2009, which issued as U.S. Pat. No. 8,771,315 on Jul. 8, 2014 and which claims the benefit of U.S. patent application Ser. No. 61/122,512, filed on Dec. 15, 2008. The disclosures of the foregoing applications are incorporated herein by reference in their entireties.

BACKGROUND

1. Field of Technology

The present disclosure relates to devices and methods for repairing tissue.

2. Related Art

Arthroscopic procedures often require soft tissue to be reattached to bone. To achieve this, anchors are placed in the bone and sutures attached to the anchor are passed through the tissue to securely retain the tissue in place. The anchors may be of a one-piece design or may be of a multiple piece design. These anchors may be made from a material that allows the anchor to be absorbed by the body over time. However, suture anchors made from such absorbable material may not allow for the tissue to be held securely against the bone during the degradation of the anchor, thereby not allowing for reattachment of the tissue to the bone. In addition, these anchors don't allow for enough surface contact between the anchor and the device used to insert the anchor into bone, thereby reducing the ability of the user from applying a high amount of torque to the anchor. As a result, the user is forced to create a hole in the bone prior to insertion of the anchor, thereby adding procedural steps and time to the surgery.

SUMMARY

In one aspect, the present disclosure relates to a composite anchor. The anchor includes a cannulated proximal portion having a threaded outer surface and a distal portion coupled to the proximal portion, the distal portion including a top portion, a bottom portion, and a through hole, wherein the top portion is configured to be disposed within the cannulation of the proximal portion.

In an embodiment, the top portion of the distal portion comprises at least two sides and a middle portion located between the at least two sides. In another embodiment, the bottom portion is substantially cone-shaped. In yet another embodiment, the at least two sides are substantially trapezoid-shaped and the middle portion is substantially round. In a further embodiment, the through hole is located in the bottom portion of the distal portion. In yet a further embodiment, the anchor further includes at least one suture disposed within the through hole and extending through the cannulation of the proximal portion.

In an embodiment, both the proximal portion and the distal portion include absorbable material. In another embodiment, the proximal portion includes absorbable material and the distal portion includes non-absorbable material. In yet another embodiment, the absorbable material includes a polymer material and the non-absorbable material includes a polymer material. In a further embodiment, the absorbable material includes a polymer material and the non-absorbable material includes a metal material.

In another aspect, the present disclosure relates to a method of repair. The method includes providing a composite anchor including a cannulated proximal portion; a distal portion coupled to the proximal portion, the distal portion including a top portion, a bottom portion, and a through hole, wherein the top portion is configured to be disposed within the cannulation of the proximal portion; and at least one suture disposed within the through hole and extending through the cannulation of the proximal portion; inserting the anchor into bone; placing soft tissue over the hole and inserting the suture through the soft tissue; and tying the suture to fixate the soft tissue to the bone.

In an embodiment, the anchor is inserted into the bone via rotary advancement of the anchor. In another embodiment, the method further includes creating a hole in the bone prior to inserting the anchor into the bone. In yet another embodiment, the proximal portion comprises a threaded outer surface.

Further areas of applicability of the present disclosure will become apparent from the detailed description provided hereinafter. It should be understood that the detailed description and specific examples, while indicating the preferred embodiment of the disclosure, are intended for purposes of illustration only and are not intended to limit the scope of the disclosure.

BRIEF DESCRIPTION OF THE DRAWINGS

The accompanying drawings, which are incorporated in and form a part of the specification, illustrate the embodiments of the present disclosure and together with the written description serve to explain the principles, characteristics, and features of the disclosure. In the drawings:

FIG. 3 shows a cross-sectional view of the proximal portion of FIG. 2.

FIG. 4 shows a perspective view of the distal portion of the composite anchor of FIG. 1.

DETAILED DESCRIPTION OF THE EMBODIMENTS

The following description of the preferred embodiment(s) is merely exemplary in nature and is in no way intended to limit the disclosure, its application, or uses.

Figure 1:
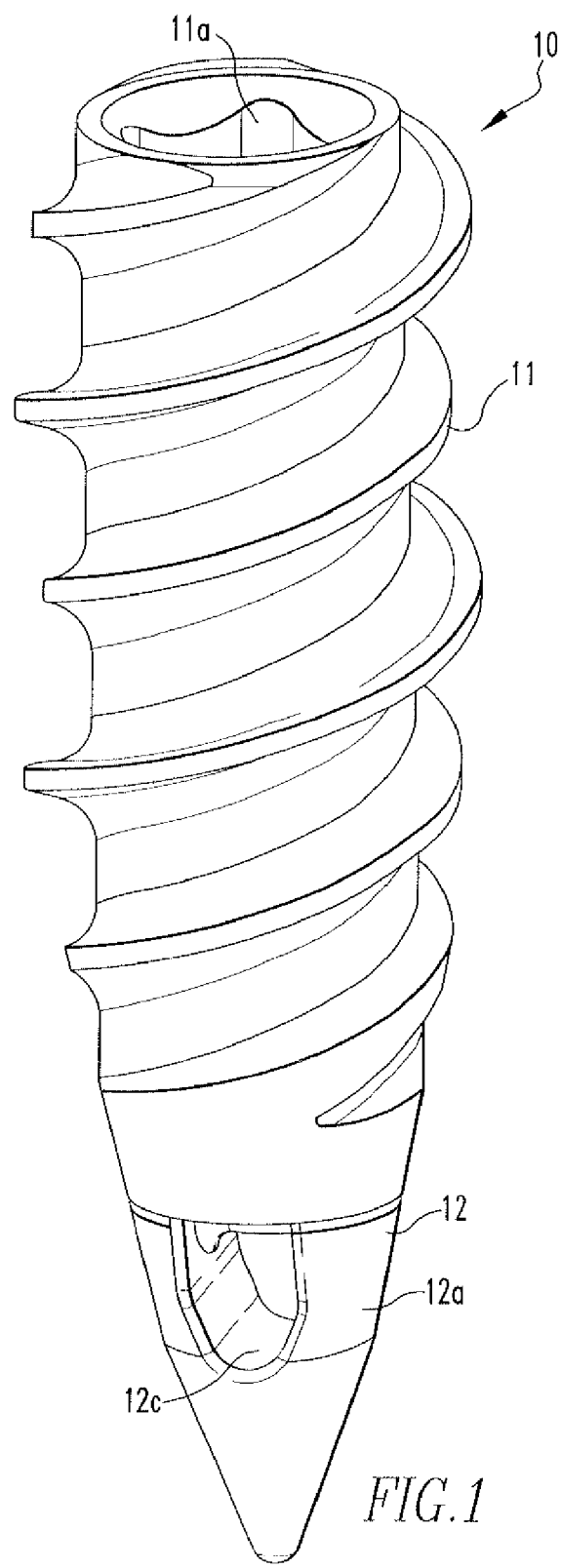
FIG. 1 shows a perspective view of the composite anchor of the present disclosure.
Figure 2:
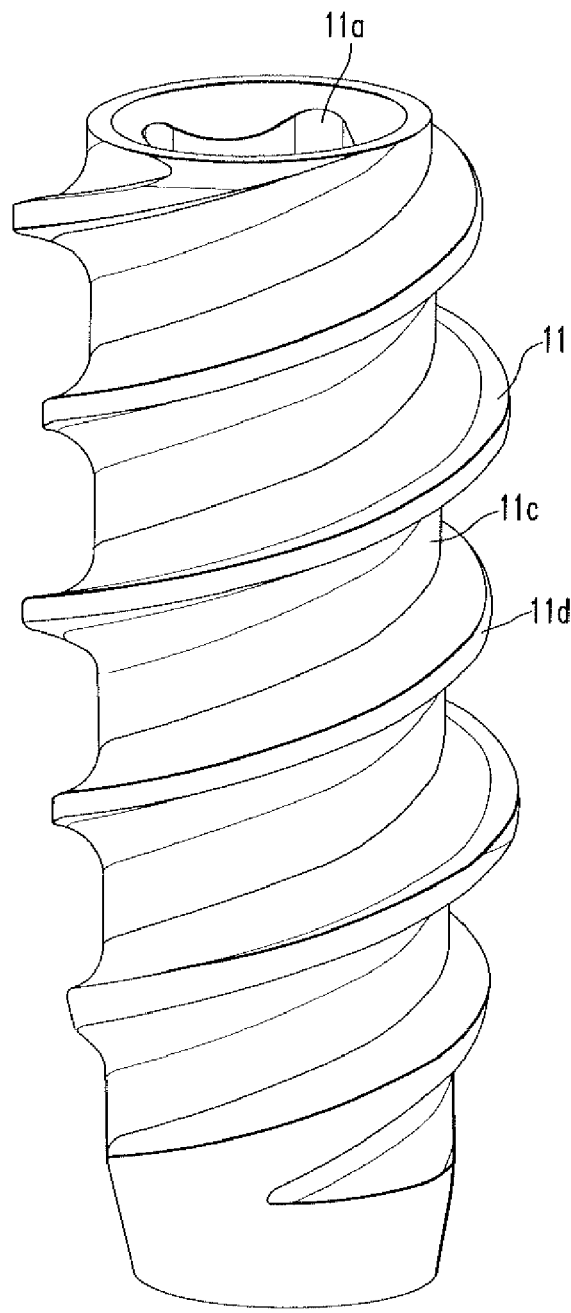
FIG. 2 shows a perspective view of the proximal portion of the composite anchor of FIG. 1.
Figure 5:
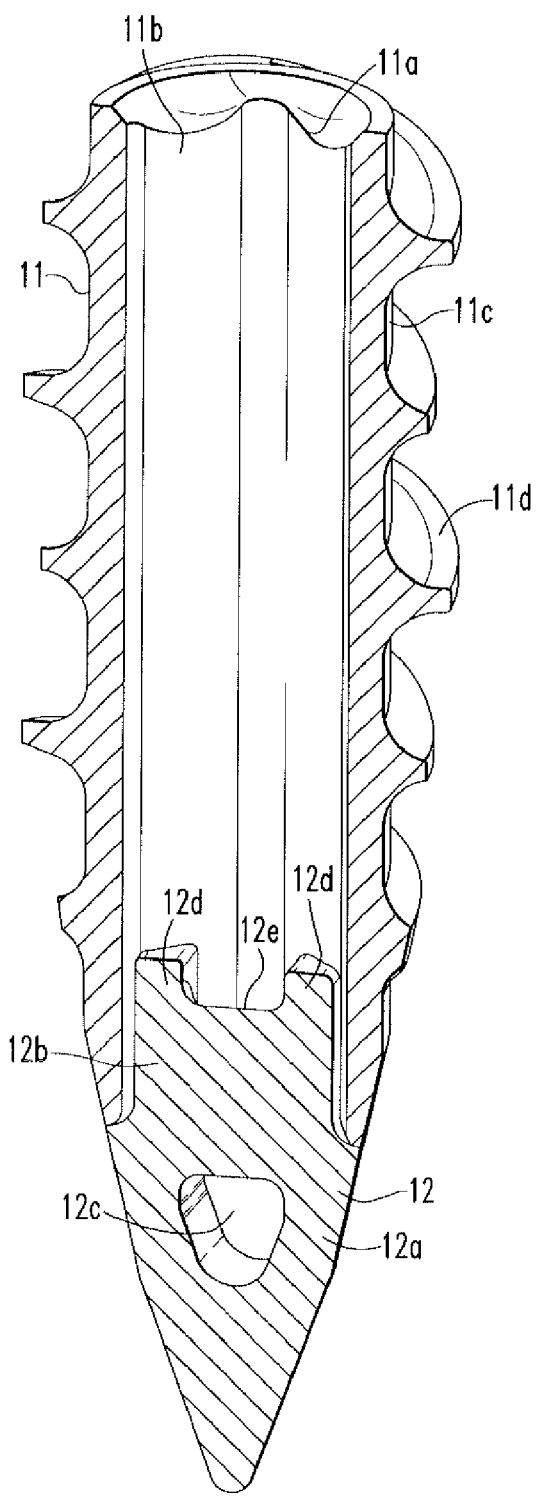
FIG. 5 shows a cross-sectional view of the composite anchor of FIG. 1.

FIGS. 1-5 show the composite anchor 10 of the present disclosure. The anchor 10 includes a proximal portion 11 and a distal portion 12 coupled to the proximal portion 11. The proximal portion 11 includes a cannulation 11a, an inner surface 11b that is configured to house the distal portion 12 and a delivery device (not shown) that is used to insert the anchor 10 into bone, as will be further described below, and an outer surface 11c that includes threads 11d. The distal portion 12 includes a bottom portion 12a, a top portion 12b, and a through hole 12c located in the bottom portion 12a. The bottom portion 12a is substantially conically-shaped to allow for easier insertion of the anchor 10 into bone, as will be further described below. The top portion 12b includes at least two sides 12d and a middle portion 12e located between the at least two sides 12d. The sides 12d are trapezoidal-shaped and the middle portion 12e is substantially rounded. As shown in FIG. 5, the shape of the sides 12d conforms to the shape of the inner surface 11b so as to allow the sides 12d to engage the inner surface 11b and thereby couple the distal portion 12 to the proximal portion 11, when the distal portion 12 is placed within the cannulation 11a of the proximal portion 11.

Figure 6A:
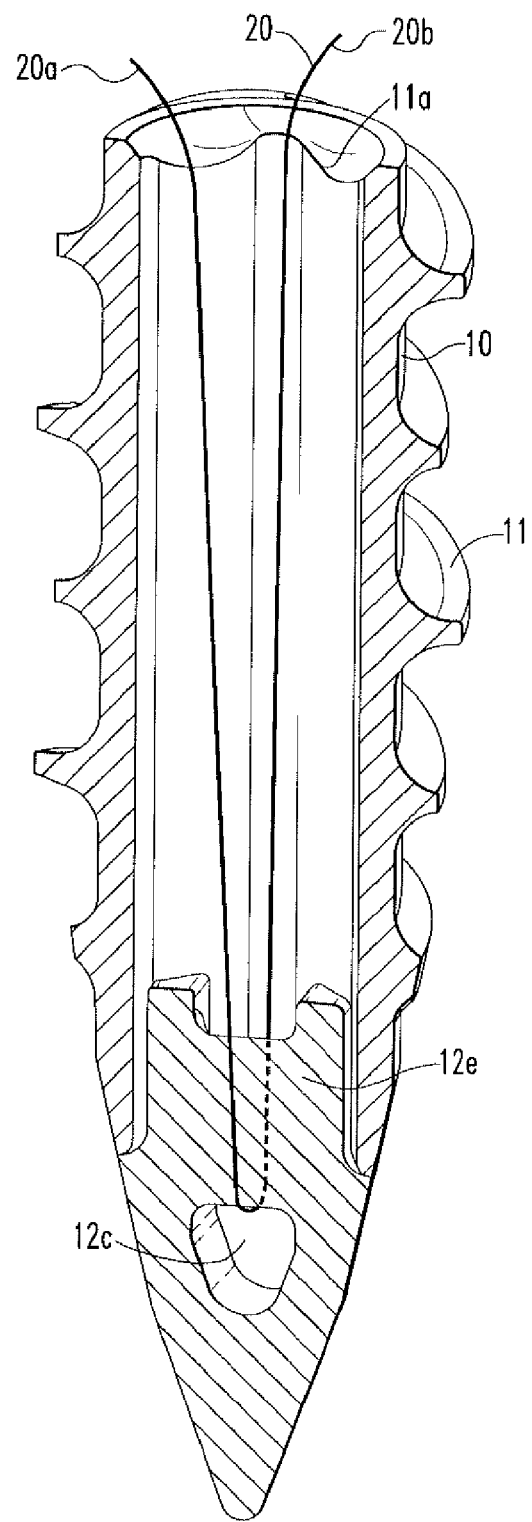
FIGS. 6A-6C show a method of repair via use of the composite anchor of FIG. 1.
Figure 6B:
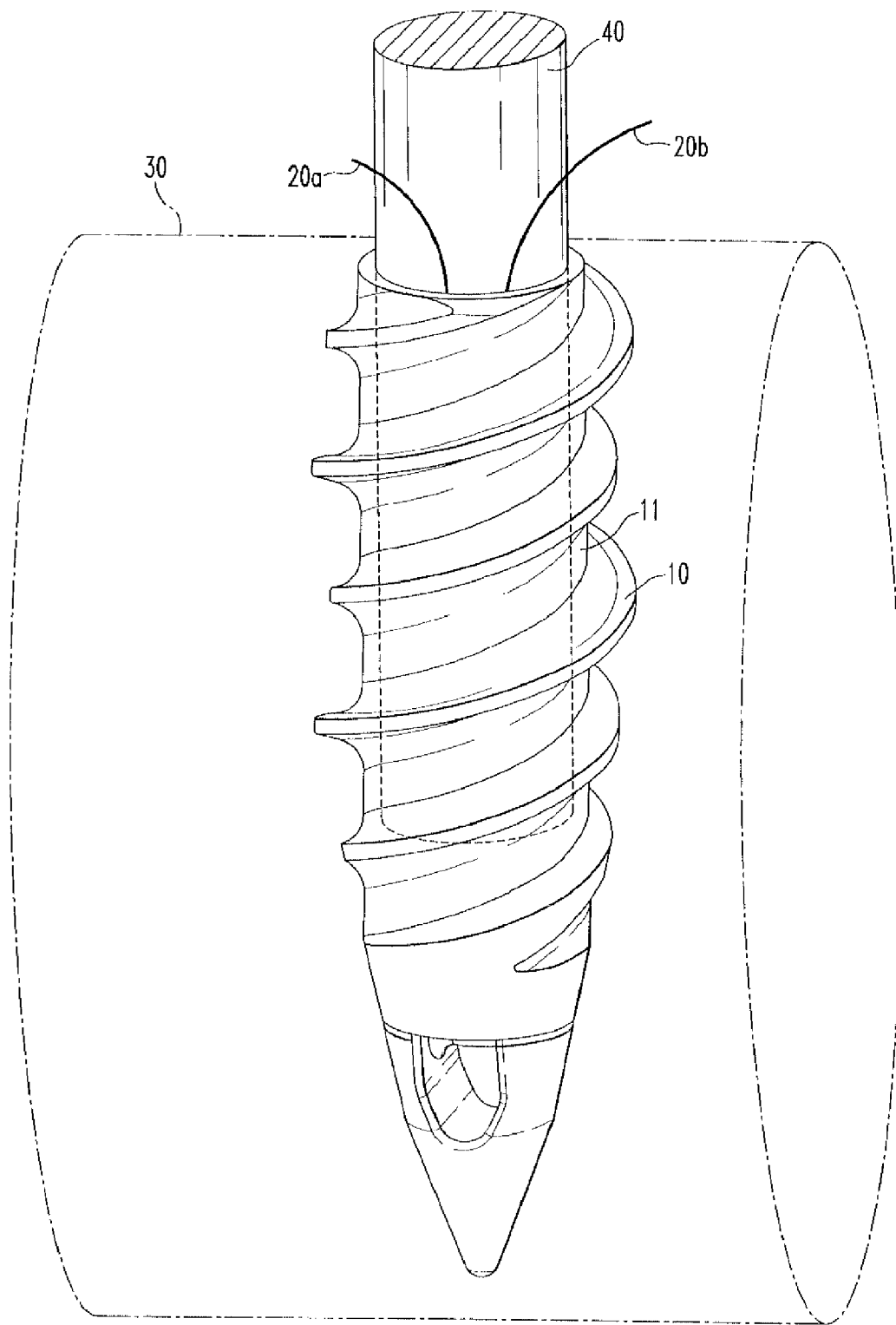
Figure 6C:
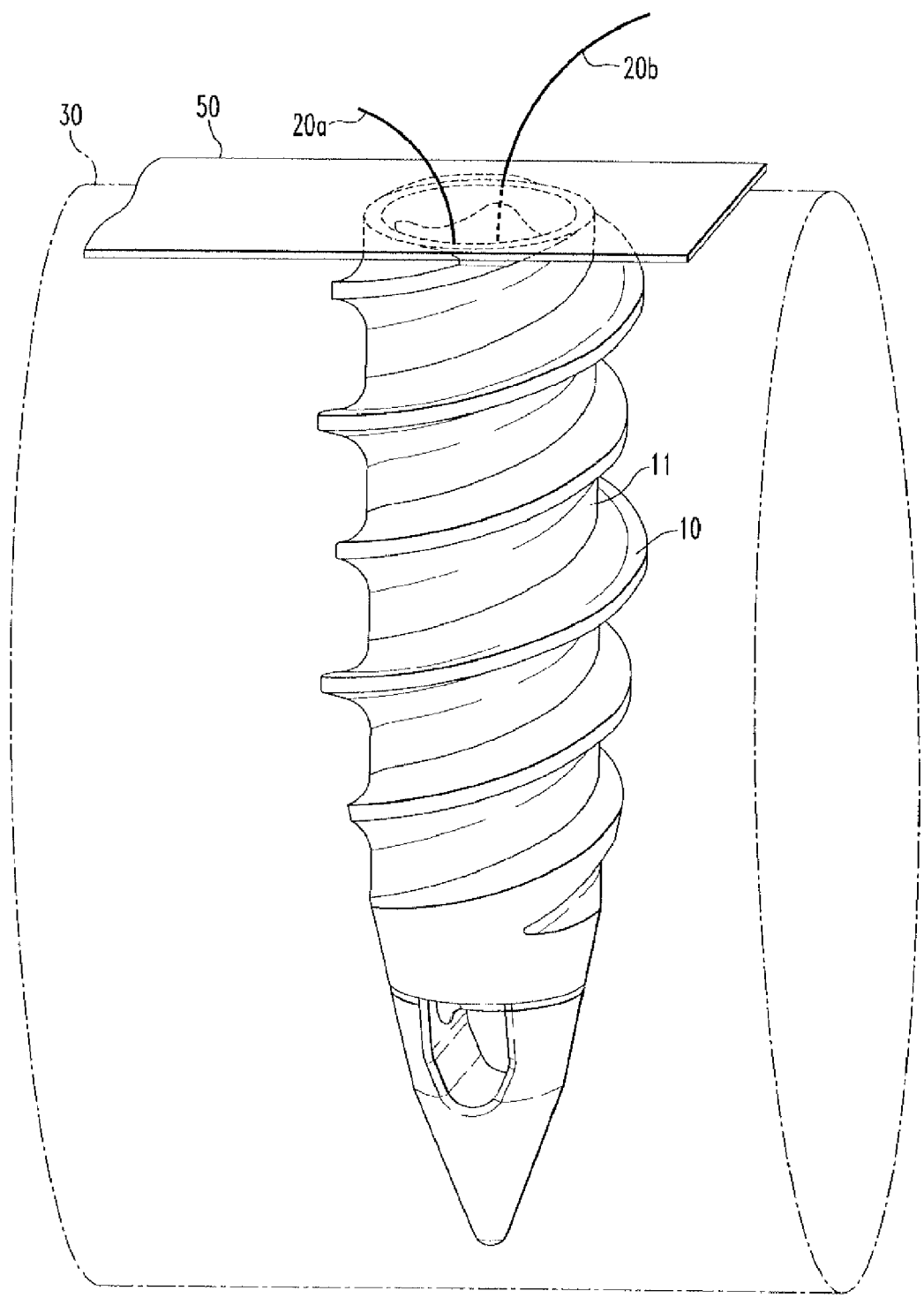

FIGS. 6A-6C show a method of repair via use of the composite anchor of the present disclosure. As shown in FIG. 6A, the anchor 10 includes at least one suture 20 housed within the through hole 12c and having ends 20a,20b extending through the cannulation 11a of the proximal portion 11 such that the suture 20 is disposed on the middle portion 12e. The anchor 10 is inserted into bone 30 via rotary advancement through use of a delivery device 40, as shown in FIG. 6B. The delivery device 40 extends a substantial length of the proximal portion 11, thereby providing a sufficient amount of surface contact between the anchor 10 and the delivery device 40 to allow the user to apply a higher amount of torque to the anchor 10 than would be allowed if the delivery device 40 extended less than a substantial length of the proximal portion 11. The ability to apply a higher amount of torque to the anchor 10 allows the user to insert the anchor 10 into the bone 30, especially hard bone, such as cortical bone, without first creating a hole in the bone 30 prior to inserting the anchor 10, thereby saving time during surgery.

After placement of the anchor 10 into the bone 30, the delivery device 40 is removed and a soft tissue 50 is placed on the bone 30 lying adjacent to the anchor 10. The suture ends 20a,20b are then inserted through the soft tissue 50 and tied to fixate the soft tissue 50 to the bone 30, as shown in FIG. 6C.

For the purposes of this disclosure, the proximal portion 11 includes an absorbable material, such as an absorbable polymer material, and the distal portion 12 includes a non-absorbable material, such as a non-absorbable polymer material or a metal material. Any absorbable polymer material may be used. An absorbable material that includes a filler, such as calcium sulfate, calcium carbonate, calcium phosphate, fibers, or other filler material that would provide for increased strength, osteoconductivity, decreased pH level of the polymer, or other benefits, may be used. A non-absorbable polymer material, such as polyetheretherketone (PEEK), or other non-absorbable polymer material could be used. Likewise, the metal material may include stainless steel, titanium, or another metal material known to one of skill in the art.

It is believed that an anchor 10 having an absorbable proximal portion 11 and a non-absorbable distal portion 12 would substantially reduce the possibility of the soft tissue 50 becoming loose during degradation of the proximal portion 11. In addition, having an anchor with a composite arrangement provides the surgeon with more selection in the type of anchor that is used during surgery. Current two piece suture anchors consist entirely of a metal material or a non-metal material.

For the purposes of this disclosure, the proximal portion 11 of the anchor 10 and the distal portion 12 of the anchor 10 are coupled via an interference fit between the proximal portion 11 and the distal portion 12. However, the components 11,12 may be coupled via ultrasonic welding or another coupling method known to one of skill in the art. In addition, it is possible for the inner surface 11b, sides 12d, the middle portion 12e, and the bottom portion 12a to have a different shape. Also, features other than threads may be present on the outer surface 11c of the proximal portion 11. Rather, the outer surface 11c may include barbs or other surface features that allow for axial advancement of the anchor 10 into the bone 30. Furthermore, more than one suture may be disposed within the through hole 12c and through the cannulation 11a. Even more, a hole may be formed in the bone 30 prior to inserting the anchor 10 into the bone 30.

As various modifications could be made to the exemplary embodiments, as described above with reference to the corresponding illustrations, without departing from the scope of the disclosure, it is intended that all matter contained in the foregoing description and shown in the accompanying drawings shall be interpreted as illustrative rather than limiting. Thus, the breadth and scope of the present disclosure should not be limited by any of the above-described exemplary embodiments, but should be defined only in accordance with the following claims appended hereto and their equivalents.

What is claimed is:

1. A method of repair comprising:
   providing a composite anchor, the composite anchor comprising:
     a cannulated proximal portion comprising a threaded outer surface and an inner surface;
     a distal portion coupled to the proximal portion, the distal portion comprising a top portion, a bottom portion, and a through hole;
     wherein the top portion is configured to be disposed within the cannulation of the proximal portion, wherein the top portion of the distal portion comprises at least two sides, and a suture bridge is formed between the at least two sides; and
     at least one suture disposed within the through hole and extending through the cannulation of the proximal portion;
   inserting the anchor into bone, wherein during such insertion, the through hole is positioned distal to the proximal portion, the through hole being in communication with the cannulation of the proximal portion to form a channel adjacent to the suture bridge;
   placing soft tissue over an entry hole of the anchor into the bone and inserting the suture through the soft tissue; and
   tying the suture to fixate the soft tissue to the bone.

2. The method of claim 1 wherein the anchor is inserted into the bone via rotary advancement of the anchor.

3. The method of claim 1 further comprising creating a hole in the bone prior to inserting the anchor into the bone.

4. The method of claim 1 wherein the bottom portion is substantially cone-shaped.

5. The method of claim 1 wherein the at least two sides are substantially trapezoid-shaped and the suture bridge is substantially round.

6. The method of claim 1 wherein both the proximal portion and the distal portion include absorbable material.

7. The method of claim 1 wherein the proximal portion includes absorbable material and the distal portion includes non-absorbable material.

8. The method of claim 7 wherein the absorbable material includes a polymer material and the non-absorbable material includes a polymer material.

9. The method of claim 7 wherein the absorbable material includes a polymer material and the non-absorbable material includes a metal material.

10. The method of claim 1 wherein the proximal portion and the distal portion are coupled by way of an interference fit.

11. The method of claim 1 wherein the proximal portion and the distal portion are coupled by way of a sonic weld.

12. The method of claim 1, wherein the distal portion provides a stop to prevent the through hole from being obscured when the top portion disposed within the cannulation of the proximal portion.

13. The method of claim 12, wherein the stop includes an annular rim defined between the top portion and the bottom portion which is configured to contact with a distal surface of the proximal portion when the top portion disposed within the cannulation of the proximal portion.

14. The method of claim 1, wherein the at least two sides of the top portion are configured to match the inner surface of the proximal portion.

15. The method of claim 1, wherein the outer surface is configured to allow for axial advancement of the anchor while inhibiting retraction of the anchor.

16. The method of claim 1, wherein the anchor is inserted into the bone such that a proximal end thereof is at least substantially flush with a surface of the bone.

17. The method of claim 1, wherein the inner surface of the proximal portion is configured to mate with a rotary tool for enabling torqueing the anchor.

18. The method of claim 17, wherein the anchor is configured to allow for the rotary tool to extend through substantially the entire length of the cannulation except for the portion of the cannulation configured for receiving the top portion.

19. The method of claim 1 wherein the anchor is inserted into the bone without creating a hole in the bone prior to such insertion.

20. The method of claim 1, wherein the suture disposed within the through hole and extending through the cannulation is able to translate even after insertion of the anchor into the bone.

* * * * *